(12) United States Patent
Bouillo et al.

(10) Patent No.: US 8,158,686 B2
(45) Date of Patent: Apr. 17, 2012

(54) USE OF COPOLYMERS AS SOLUBILIZERS FOR SLIGHTLY WATER-SOLUBLE COMPOUNDS

(75) Inventors: Nathalie Bouillo, Baden-Baden (DE); Marianna Pierobon, Ludwigshafen (DE); Ralf Widmaier, Mannheim (DE); Rainer Dobrawa, Mannheim (DE); Kathrin Meyer-Boehm, Feucht (DE); Ronald Frans-Maria Lange, Ludwigshafen (DE)

(73) Assignee: BASF SE (DE)

( * ) Notice: Subject to any disclaimer, the term of this patent is extended or adjusted under 35 U.S.C. 154(b) by 697 days.

(21) Appl. No.: 12/092,676

(22) PCT Filed: Oct. 25, 2006

(86) PCT No.: PCT/EP2006/067747
§ 371 (c)(1),
(2), (4) Date: May 5, 2008

(87) PCT Pub. No.: WO2007/051743
PCT Pub. Date: May 10, 2007

(65) Prior Publication Data
US 2008/0293828 A1 Nov. 27, 2008

(30) Foreign Application Priority Data
Nov. 4, 2005 (DE) .......................... 10 2005 053 066

(51) Int. Cl.
A61K 47/30 (2006.01)
A61K 31/33 (2006.01)
A01N 43/00 (2006.01)

(52) U.S. Cl. .................................... 514/772.3; 514/183

(58) Field of Classification Search .................. 514/183, 514/772.3
See application file for complete search history.

(56) References Cited

U.S. PATENT DOCUMENTS

| | | | |
|---|---|---|---|
| 3,767,587 A * | 10/1973 | Claussen et al. ......... | 252/301.23 |
| 4,894,236 A * | 1/1990 | Embry et al. ................ | 424/486 |
| 4,904,408 A * | 2/1990 | Kud et al. ..................... | 510/360 |
| 5,013,556 A | 5/1991 | Woodle et al. | |
| 5,552,159 A * | 9/1996 | Mueller et al. ................ | 424/464 |
| 5,580,938 A | 12/1996 | Gutweiler et al. | |
| 5,631,018 A | 5/1997 | Zalipsky et al. | |
| 6,075,107 A | 6/2000 | Korhrade et al. | |
| 6,107,397 A | 8/2000 | Blankenburg et al. | |
| 6,271,307 B1 * | 8/2001 | Huff et al. ...................... | 525/61 |
| 6,331,294 B1 | 12/2001 | Meffert et al. | |
| 6,350,398 B1 * | 2/2002 | Breitenbach et al. ......... | 264/129 |
| 6,497,867 B2 | 12/2002 | Meffert et al. | |
| 6,770,293 B2 | 8/2004 | Angel et al. | |
| 6,783,770 B2 * | 8/2004 | Angel et al. .................. | 424/451 |
| 6,867,262 B1 | 3/2005 | Angel et al. | |
| 2001/0036471 A1 * | 11/2001 | Angel et al. .................. | 424/451 |
| 2002/0119169 A1 * | 8/2002 | Angel et al. .................. | 424/400 |
| 2003/0224025 A1 | 12/2003 | Gotsche et al. | |
| 2006/0142499 A1 | 6/2006 | Guntherberg et al. | |
| 2006/0235119 A1 | 10/2006 | Schmalz et al. | |
| 2008/0293828 A1 | 11/2008 | Bouillo et al. | |
| 2008/0300320 A1 | 12/2008 | Lange et al. | |
| 2009/0036550 A1 | 2/2009 | Bouillo et al. | |
| 2010/0204425 A1 | 8/2010 | Mertoglu et al. | |

FOREIGN PATENT DOCUMENTS

| | | |
|---|---|---|
| CA | 2 082 573 | 11/1992 |
| DE | 2016470 | 10/1971 |
| DE | 3228384 A1 | 2/1984 |
| DE | 19712247 A1 | 10/1998 |
| DE | 19935063 A1 | 2/2001 |
| EP | 0285038 B1 | 10/1988 |
| EP | 0544144 B1 | 6/1993 |
| EP | 876819 | 11/1998 |
| EP | 0948957 BI | 3/1999 |
| EP | 0953347 A2 | 3/1999 |
| EP | 1136070 B1 | 3/2001 |
| EP | 1138322 B1 | 3/2001 |
| EP | 1674485 A1 | 6/2006 |
| WO | WO-9420073 | 9/1994 |
| WO | WO-9519759 | 7/1995 |
| WO | WO-01/09271 A1 | 2/2001 |
| WO | WO 02/15865 | 2/2002 |
| WO | WO-03072158 | 9/2003 |
| WO | WO-2007/051743 A2 | 5/2007 |

OTHER PUBLICATIONS

STN Registry No. 25322-68-3 (Copyright ACS on STN, entered into STN on Nov. 16, 1984), 14 pages.*
Chemical Book, N-Vinylcaprolactam [downloaded Dec. 10, 2010] [Retrieved from <URL: http://www.chemicalbook.com/ChemicalProductProperty_EN_CB4341084.htm>], 2 pages.*
MedlinePlus, U.S. National Library of Medicine NIH National Institutes of Health, Beta-carotene, [downloaded Dec. 9, 2010] [Retrieved from <URL: http://www.nlm.nih.gov/medlineplus/druginfo/natural/999.htm>], 1 page.* Fisher Scientific, Material Safety Data Sheet, Beta-Carotene, 99% (UV-VIS) [downloaded Dec. 8, 2010] [Retrieved from internet <URL: http://fscimage.fishersci.com/msds/17503>], 5 pages.*
Sigma-Aldrich, Hydrophobic Polymers [downloaded Dec. 13, 2010] [Retrieved from internet <URL: http://www.sigmaaldrich.com/materials-science/material-science-products.html?TablePage=16372120.], 1 page.*
Sigma-Aldrich, Vinyl Esters [downloaded Dec. 13, 2010] [Retrieved from internet <URL: http://www.sigmaaldrich.com/materials-science/material-sicnece-products.html?TablePage=20203021>], 2 pages.*
Aldrich, Reference: Polymer Properties [downloaded Dec. 13, 2010] [Retrieved from Internet <URL: http://sigmaaldrich.com/etc/medialib/docs/Aldrich/General_Informaiton/viscosity.Par.0001.File.tmp/viscosity.pdf>], 2 pages.*
About.com, K-Value [downloaded Dec. 10, 2010] [Retrieved from internet <URL: http://composite.about.com/library/glossary/k/bldef-k29877.htm>], 1 page.*
Dow, Dow Wolff Cellulosics, Nitrocellulose, 822-00007-0708, pp. 1, 51, 60; 3 pages.*

(Continued)

Primary Examiner — Tracy Vivlemore
Assistant Examiner — Miriam A. Levin
(74) Attorney, Agent, or Firm — Connolly Bove Lodge & Hutz LLP

(57) ABSTRACT

The use of copolymers obtained by free-radical polymerization of a mixture of
  i) 30 to 80% by weight of N-vinyllactam,
  ii) 10 to 50% by weight of vinyl acetate, and
  iii) 10 to 50% by weight of a polyether,
with the proviso that the total of components i), ii) and iii) equals 100% by weight,
as solubilizers for slightly water-soluble substances.

13 Claims, No Drawings

OTHER PUBLICATIONS

W.V. Titow, PVC Technology 4th Ed., Elsevier Applied Science Pubilshers Ltd. 1984, reprinted 1986 [excerpt downloaded Dec. 13, 2010] [ Retrieved from internet <URL: http://books.google.com/books?id=N79YwkVx4wC&pg=PA43&lpg=PA43&dq=Fikentscher+k+value&source=bl&ots=4HdSLOFjeM&sig=RGyS9xqTHSDZbYGkllRVfPOsGb0&hl=en&ei=8_QGTY_5O4aglAeXzrC4Dg&sa=X&oi=book_result&ct=result&resnum+10&ved=0CFUQ6AEwCQ#v=onepage&q=Fikentscher%20%20value&f=false>], 5 pages.*

Zeus Industrial Products, Inc., Technical Whitepaper, Friction and Wear of Polymers [downloaded Dec. 13, 2010] [Retrieved from internet <URL: http://www.zeusinc.com/UserFiles/zeusinc/Documents/Zeus_Friction.pdf>], 9 pages.*

ASTEC, K-Value and R-Value of ASTEC compared with mass insulation, F.A.Q. [downloaded Dec. 13, 2010] [Retrieved from internet <URL: http://www.icc-astec.com/faq/thermal-values.php>], 2 pages.*

W.V. Titow, PVC Technology 4th Ed., Elsevier Applied Science Pubilshers Ltd. 1984, reprinted 1986 [excerpt downloaded Dec. 13, 2010] [ Retrieved from internet <URL: http://books.google.com/books?id=N79YwkVx4wC&pg=PA43&lpg=PA43&dq=Fikentscher+k+value&source=bl&ots=4HdSLOFjeM&sig=RGyS9xqTHSDZbYGkllRVfPOsGb0&hl=en&ei=8_QGTY_5O4aglAeXzrC4Dg&sa=X&oi=book_result&ct=result&resnum+10&ved=0CFUQ6AEwCQ#v=onepage&q=Fikentscher%20%20value&f=false>], 5 pages.*

Dr. Richard Clarkson, Chemistry Rules, Junior Part—Organic Chemistry—Alkenes, updated Oct. 30, 2005 [downloaded Dec. 17, 2010] [Retrieved from internet <URL: http://www.chemistryrules.me.uk/junior/organic.html>], 5 pages.*

Cliffs Notes, Reactions of Alcohols [downloaded Dec. 16, 2010] [Retrieved from internet <URL: http://cliffnotes.com/study_guide/topicArticleId-23297.articleId23272], 11 pages.*

Cliffs Notes, Reactions of Ethers [downloaded Dec. 17, 2010] [Retrieved from internet <URL: http://cliffnotes.com/study_guide/topicArticleld-23297,articleld-23275.html>], 3 pages.*

Kang Moo Huh, et al., PLGA-PEG Block Copolymers for Drug Formulations, Drug Delivery, Issue Date: vol. 3, No. 5 (issue date Jul./Aug. 2003; posted Mar. 28, 2008), 10 pages.*

Andrew G. West, et al., Poly(ethylene glycol) as a "green solvent" forRAFT polymerization of methyl methacrylate, Polymer 51, Elsevier, Ltd. (2010) 3836-3842, 7 pages.*

LookChem, CAS No. 9004-65-3, Hydroxypropylmethylcellulose Suppliers, MSDS download [Downloaded Dec. 19, 2010] [Retrieved from internet <URL: http://www.lookchem.com/cas-900/9004-65-3.html?p=2.], 4 pages.*

Gelatin, [Downloaded Dec. 19, 2010] [Retrieved from <URL: http://www.boith.com/food%20and%20feed%20product.files/Edible%20Gelatin.html>], 4 pages.*

Hispanagar, Material Safety Data Sheet, Carrageenan [downloaded Dec. 19, 2010] [Retrieved from internet <URL: http:www.globalingredients.com/pdf/MSDS%20Carrageenan.pdf>], 4 pages.*

International Preliminary Report on Patentability, PCT/EP2006/067747 (Jul. 8, 2008), 9 pages.*

Rauwendaal, "Encyclopedia of polymer science and technol.," Wiley, 2002, vol. 2, pp. 497-558.

Wang, "Polymer Extrusion Devotatilization," Chem. Eng. Technol., 2001, vol. 24, pp. 957-961.

* cited by examiner

USE OF COPOLYMERS AS SOLUBILIZERS FOR SLIGHTLY WATER-SOLUBLE COMPOUNDS

This application is a National Stage Application of PCT/EP2006/067747, filed Oct. 25, 2006 and claims priority to application DE 102005053066.4, filed Nov. 4, 2005, the entire disclosures of which are incorporated herein by reference.

The present invention relates to the use of copolymers which are obtained by polymerizing vinyl acetate and N-vinyllactams in the presence of a polyether as solubilizers for slightly water-soluble substances, and to the corresponding preparations.

In the production of homogeneous preparations in particular of bioactive substances, solubilization of hydrophobic, i.e. slightly water-soluble substances, has become of very great practical importance.

Solubilization means making substances which are slightly soluble or insoluble in a particular solvent, especially water, soluble by surface-active compounds, the solubilizers. Such solubilizers are able to convert substances of low or zero solubility in water into clear, or at most opalescent, aqueous solutions without altering the chemical structure of these substances (cf. Römpp Chemie Lexikon, 9th edition, Vol. 5. p. 4203, Thieme Verlag, Stuttgart, 1992).

The produced solubilizates are characterized by the substance of low or zero solubility in water being in the form of a colloidal solution in the aggregates of molecules of the surface-active compounds which form in aqueous solution, such as, for example, hydrophobic domains or micells. The resulting solutions are stable or metastable single-phase systems which appear optically clear or opalescent.

Solubilizers may for example improve the appearance of cosmetic formulations and of food preparations by making the formulations transparent. In the case of pharmaceutical preparations, there may additionally be an increase in the bioavailability and thus the effect of drugs through the use of solubilizers.

The solubilizers employed for pharmaceutical drugs and cosmetic active substances are mainly surfactants such as ethoxylated castor oil or ethoxylated hydrogenated castor oil, ethoxylated sorbitan fatty acid esters or ethoxylated hydroxystearic acid.

However, the solubilizers described above and employed to date show a number of technical disadvantages when used.

The solubilizing effect of known solubilizers is only low for some slightly soluble drugs such as, for example, clotrimazole.

EP-A 876 819 describes the use of copolymers of at least 60% by weight of N-vinyl-pyrrolidone and amides or esters with long-chain alkyl groups.

EP-A 948 957 describes the use of copolymers of monoethylenically unsaturated carboxylic acids such as, for example, acrylic acid and hydrophobically modified comonomers such as, for example N-alkyl- or N,N-dialkylamides of unsaturated carboxylic acids with $C_8$-$C_{30}$-alkyl radicals.

DE-A 199 350 63 discloses polyalkylene oxide-containing graft copolymers based on vinyllactams and vinyl acetate, and the use thereof as gas hydrate inhibitors.

EP-A 953 347 discloses the use of polyalkylene oxide-containing graft copolymers as solubilizers. The graft copolymers described therein and composed of vinyl acetate and polyalkylene oxides are frequently not powders but glutinous liquids, which is a technical disadvantage during use.

A further desirable requirement is for solubilizers to be able to form so-called "solid solutions" with slightly soluble substances. The term "solid solution" refers to a state in which a substance is in the form of a microdispersion or, in the ideal case, a molecular dispersion in a solid matrix, for example, a polymer matrix. Such solid solutions result, for example when used in the solid pharmaceutical dosage forms of a slightly soluble active ingredient, in an improved release of the active ingredient. An important requirement is that such solid solutions be stable if stored even for a prolonged period, i.e. that the active ingredient does not crystallize out. Also important is the capacity of the solid solution, in other words the ability to form stable solid solutions with maximum content of active ingredients.

An important part is played in the formation of solid solutions not only by the fundamental ability of the solubilizers to form solid solutions but also by the hygroscopicity of the solubilizers. Solubilizers which absorb too much water from the ambient air lead to liquefactions of the solid solution and to unwanted crystallization of the active ingredients. A hygroscopicity which is too great may also cause problems in processing to dosage forms.

Previously disclosed polymeric solubilizers have the disadvantage that they either do not form stable solid solutions. There is moreover room for improvement in relation to solubilization in aqueous systems. Some of the known solubilizers also have disadvantages in relation to processability because of their tendency to tackiness, because they do not represent sufficiently free-flowing powders.

The object therefore was to provide novel and improved solubilizers for applications in pharmaceuticals, cosmetics, food technology, agricultural technology or other industries not having the described disadvantages.

The object has been achieved according to the invention by the use of water-soluble or water-dispersible copolymers which are obtained by free-radical polymerization of a mixture of i) 30 to 80% by weight of N-vinyllactam,
ii) 10 to 50% by weight of vinyl acetate and
iii) 10 to 50% by weight of a polyether, with the proviso that the total of i), ii) and iii) equals 100% by weight.

According to one embodiment of the invention, preferred polymers are obtained from:

i) 30 to 70% by weight of N-vinyllactam
ii) 15 to 35% by weight of vinyl acetate, and
iii) 15 to 35% by weight of a polyether, and particularly preferred polymers from:

i) 40 to 60% by weight of N-vinyllactam
ii) 15 to 35% by weight of vinyl acetate
iii) 15 to 30% by weight of a polyether.

In a further embodiment of the invention, preferred polymers comprise from 10 to 35% by weight of a polyether.

Particularly preferred polymers are composed of i) 40 to 60% by weight of N-vinyllactam
ii) 15 to 35% by weight of vinyl acetate
iii) 10 to 30% by weight of polyether.

The proviso that the total of components i), ii) and iii) equals 100% by weight also applies to the preferred and particularly preferred compositions.

A suitable N-vinyllactam is N-vinylcaprolactam or N-vinylpyrrolidone or mixtures thereof. N-Vinylcaprolactam is preferably used.

Suitable and preferred polyethers are polyalkylene glycols. The polyalkylene glycols may have molecular weights of from 1000 to 100 000 D [daltons], preferably 1500 to 35 000 D, particularly preferably 1500 to 10 000 D. The molecular weights are determined on the basis of the OH number measured as specified in DIN 53240.

Polyethylene glycols are suitable and particularly preferred polyalkylene glycols. Also suitable are polypropylene glycols, polytetrahydrofurans or polybutylene glycols which are obtained from 2-ethyloxirane or 2,3-dimethyloxirane.

Suitable polyethers are also random or block copolymers of polyalkylene glycols obtained from ethylene oxide, propylene oxide and butylene oxides, such as, for example, polyethylene glycol-polypropylene glycol block copolymers. The block copolymers may be of the AB or ABA type.

Preferred polyalkylene glycols also include those alkylated on one or both terminal OH groups. Suitable alkyl radicals are branched or unbranched $C_1$- to $C_{22}$-alkyl radicals, preferably $C_1$-$C_{18}$-alkyl radicals, for example methyl, ethyl, n-butyl, isobutyl, pentyl, hexyl, octyl, nonyl, decyl, dodecyl, tridecyl or octadecyl radicals.

General processes for preparing the copolymers of the invention are known per se. The preparation takes place by free-radical polymerization, preferably solution polymerization, in nonaqueous organic solvents or in mixed nonaqueous/aqueous solvents.

Suitable nonaqueous organic solvents are, for example, alcohols such as methanol, ethanol, n-propanol and isopropanol, and glycols such as ethylene glycol and glycerol.

Further suitable solvents are esters such as, for example, ethyl acetate, n-propyl acetate, isopropyl acetate, isobutyl acetate or butyl acetate.

The polymerization is preferably carried out at temperatures from 60 to 100° C.

Free-radical initiators are employed to initiate the polymerization. The amounts of initiator or initiator mixtures used, based on monomer employed, are between 0.01 and 10% by weight, preferably between 0.3 and 5% by weight.

Depending on the nature of the solvent used, both organic and inorganic peroxides are suitable, such as sodium persulfate or azo initiators such as azobisisobutyronitrile, azo-bis(2-amidopropane) dihydrochloride or 2,2'-azobis(2-methylbutyronitrile).

Examples of peroxide initiators are dibenzoyl peroxide, diacetyl peroxide, succinyl peroxide, tert-butyl perpivalate, tert-butyl perethylhexanoate, tert-butyl perneodecanoate, tert-butyl permaleate, bis-(tert-butylper)cyclohexane, tert-butylperisopropyl carbonate, tert-butyl peracetate, 2,2-bis(tert-butylper)butane, dicumyl peroxide, di-tert-amyl peroxide, di-tert-butyl peroxide, p-menthane hydroperoxide, pinane hydroperoxide, cumene hydroperoxide, tert-butyl hydroperoxide, hydrogen peroxide and mixtures of said initiators. Said initiators can also be used in combination with redox components such as ascorbic acid.

Particularly suitable initiators are tert-butyl perneodecanoate, tert-butyl perpivalate or tert-butyl perethylhexanoate.

The free-radical polymerization can place if appropriate in the presence of emulsifiers, if appropriate further protective colloids, if appropriate molecular weight regulators, if appropriate buffer systems and if appropriate subsequent pH adjustment using bases or acids.

Suitable molecular weight regulators are sulfhydryl compounds such as alkyl mercaptans, e.g. n-dodecyl mercaptan, tert-dodecyl mercaptan, thioglycolic acid and esters thereof, mercaptoalkanols such as mercaptoethanol. Further suitable regulators are mentioned for example in DE 197 12 247 A1, page 4. The necessary amount of the molecular weight regulators is in the range from 0 to 5% by weight based on the amount of (co)monomers to be polymerized. If regulators are used, the amount employed is in particular in the range from 0.05 to 2% by weight, particularly preferably 0.1 to 1.5% by weight. However, polymerization in the absence of a regulator is very particularly preferred.

It is also possible if appropriate to use emulsifiers, for example ionic or nonionic surfactants whose HLB is normally in the range from 3 to 13. For the definition of HLB, reference is made to the publication by W. C. Griffin, J. Soc. Cosmetic Chem., Volume 5, 249 (1954). The amount of surfactants, based on the polymer can be from 0 to 10% by weight, preferably 0 to 5% by weight.

The monomer, or the monomer mixture or the emulsion of monomer(s) are introduced together with the initiator, which is generally present in solution, into a stirred reactor at the polymerization temperature (batch process) or if appropriate metered continuously or in a plurality of consecutive stages into the polymerization reactor (feed process). It is usual in the feed process for the reactor to be charged, before the start of the actual polymerization, besides the solvent (in order to make stirring of the reaction mixture possible) also with partial quantities, rarely the total quantity intended for the polymerization, of the starting materials such as emulsifiers, protective colloids, monomers, regulators etc. or partial quantities of the feeds (generally monomer feed or emulsion feed and initiator feed).

The polymerization can be carried out both under atmospheric pressure and in a closed reactor under elevated pressure. In this case it is possible to polymerize either under the pressure set up during the reaction, or the pressure can be adjusted by injecting a gas or evacuating. The pressure can also be controlled by partial decompression of the reactor into the condenser.

A nonaqueous solvent used for the polymerization can subsequently be removed and replaced by water by steam distillation. This normally entails initially the nonaqueous solvent being distilled out pure as far as possible and then being completely replaced by water by passing in steam.

After the polymerization it is possible to employ generally known processes for reducing residual monomers. Examples of such processes are further addition of an initiator at the end of the polymerization, hydrolysis of vinyllactam monomers by adding acids, treatment of the polymer solution with solid phases such as ion exchangers, feeding in a monomer which copolymerizes well, membrane filtration and further customary methods.

The solids content of the resulting aqueous polymer dispersions or solutions is usually from 10 to 70% by weight, preferably 15 to 60% by weight, particularly preferably 15 to 40% by weight.

The polymer dispersions or solutions can be converted into powder form or into granules by various drying processes such as, for example, spray drying, fluidized spray drying, drum drying, paddle drying, belt drying or freeze drying. It may be advisable during the spray drying to add additives such as, for example, colloidal silica or hydrophobically modified colloidal silica.

The copolymers are obtained as aqueous dispersions or aqueous solutions or, after removal of the water content, as very free-flowing, water-dispersible or water-soluble powders.

The polymers have Fikentscher K values in the range from 10 to 60, preferably 15 to 40, measured in a 1% by weight ethanolic solution.

Applications:

The copolymers to be used according to the invention can be employed in principle in all areas where substances of only low or zero solubility in water are either intended to be employed in aqueous preparations or intended to display their effect in aqueous medium. The copolymers are accordingly used as solubilizers for slightly water-soluble substances, in particular bioactive substances.

The term "slightly water-soluble" includes according to the invention also practically insoluble substances and means that at least 30 to 100 g of water are required per g of substance for the substance to dissolved in water at 20° C. In the case of practically insoluble substances, at least 10 000 g of water are required per g of substance.

In the context of the present invention, slightly water-soluble bioactive substances mean active pharmaceutical ingredients for humans and animals, cosmetic or agrochemical active substances or dietary supplements or dietetic active substances.

Further slightly soluble substances suitable for solubilization are also colorants such as inorganic or organic pigments.

The present invention provides in particular amphiphilic compounds for use as solubilizers for pharmaceutical and cosmetic preparations and for food preparations. They have the property of solubilizing slightly soluble active ingredients in the area of pharmacy and cosmetics, slightly soluble dietary supplements, for example vitamins and carotenoids, but also slightly soluble active substances for use in crop protection agents and veterinary medical active ingredients.
Solubilizers for Cosmetics:

The copolymers can be employed according to the invention as solubilizers in cosmetic formulations. They are suitable for example as solubilizers for cosmetic oils. They have a good solubilizing capacity for fats and oils such as peanut oil, jojoba oil, coconut oil, almond oil, olive oil, palm oil, castor oil, soybean oil or wheatgerm oil or for essential oils such as dwarf pine oil, lavender oil, rosemary oil, spruce needle oil, pine needle oil, eucalyptus oil, peppermint oil, sage oil, bergamot oil, terpentine oil, melissa oil, sage oil, juniper oil, lemon oil, anise oil, cardamom oil, peppermint oil, camphor oil etc. or for mixtures of these oils.

The polymers of the invention can further be used as solubilizers for UV absorbers which are slightly soluble or insoluble in water, such as, for example, 2-hydroxy-4-methoxybenzophenone (Uvinul® M 40, from BASF), 2,2',4,4'-tetrahydroxy-benzophenone (Uvinul® D 50), 2,2'-dihydroxy-4,4'-dimethoxybenzophenone (Uvinul® D49), 2,4-dihydroxybenzophenone (Uvinul® 400), 2'-ethylhexyl 2-cyano-3,3-diphenylacrylate (Uvinul® N 539), 2,4,6-trianilino-p-(carbo-2'-ethylhexyl-1'-oxy)-1,3,5-triazine (Uvinul® T 150), 3-(4-methoxybenzylidene)camphor (Eusolex® 6300, from Merck), 2-ethylhexyl N,N-dimethyl-4-aminobenzoate (Eusolex® 6007), 3,3,5-trimethylcyclohexyl salicylate, 4-isopropyldibenzoylmethane (Eusolex® 8020), 2-ethylhexyl p-methoxycinnamate and 2-isoamyl p-methoxycinnamate, and mixtures thereof.

The present invention therefore also relates to cosmetic preparations which comprise at least one of the copolymers of the invention having the composition stated at the outset as solubilizers. Preferred preparations are those which, besides the solubilizer, comprise one or more slightly soluble cosmetic active substances, for example the abovementioned oils or UV absorbers.

These formulations are water- or water/alcohol-based solubilizates. The solubilizers of the invention are employed in the ratio of from 0.2:1 to 20:1, preferably 1:1 to 15:1, particularly preferably 2:1 to 12:1, to the slightly cosmetic active substance.

The content of solubilizer of the invention in the cosmetic preparation is in the range from 1 to 50% by weight, preferably 3 to 40% by weight, particularly preferably 5 to 30% by weight, depending on the active substance.

It is possible in addition for further auxiliaries to be added to this formulation, for example nonionic, cationic or anionic surfactants such as alkyl polyglycosides, fatty alcohol sulfates, fatty alcohol ethersulfates, alkanesulfonates, fatty alcohol ethoxylates, fatty alcohol phosphates, alkylbetaines, sorbitan esters, POE-sorbitan esters, sugar fatty acid esters, fatty acid polyglycerol esters, fatty acid partial glycerides, fatty acid carboxylates, fatty alcohol sulfosuccinates, fatty acid sarcosinates, fatty acid isethionates, fatty acid taurinates, citric acid esters, silicone copolymers, fatty acid polyglycol esters, fatty acid amides, fatty acid alkanolamides, quaternary ammonium compounds, alkylphenol ethoxylates, fatty amino ethoxylates, cosolvents such as ethylene glycol, propylene glycol, glycerol and others.

Further ingredients which may be added are natural or synthetic compounds, e.g. lanolin derivatives, cholesterol derivatives, isopropyl myristate, isopropyl palmitate, electrolytes, colorants, preservatives, acids (e.g. lactic acid, citric acid).

These formulations are Used for example in bath additives such as bath oils, aftershaves, face tonics, hair tonics, eau de cologne, eau de toilette and in sunscreen compositions. A further area of use is the oral care sector, for example in mouthwashes, toothpastes, denture adhesive creams and the like.

The copolymers are also suitable for industrial applications for example for preparations of slightly soluble coloring agents, in toners, preparations of magnetic pigments and the like.
Description of the Solubilization Method:

The copolymers of the invention can be employed for preparing solubilizates for cosmetic formulations either as 100% pure substance or, preferably, as aqueous solution.

Normally, the solubilizers will be dissolved in water and vigorously mixed with the slightly soluble cosmetic active substance to be used in each case.

However, it is also possible for the solubilizer to be mixed vigorously with the slightly soluble cosmetic active substance to be used in each case and then for demineralized water to be added while stirring continuously.
Solubilizers for Pharmaceutical Applications:

The claimed copolymers are likewise suitable for use as solubilizer in pharmaceutical preparations of any type which may comprise one or more drugs which are slightly soluble or insoluble in wafer, and vitamins and/or carotenoids. Aqueous solutions or solubilizates for oral administration are of particular interest in this connection. Thus, the claimed copolymers are suitable for use in oral dosage forms such as tablets, capsules, powders, solutions. In these they may increase the bioavailability of the slightly soluble drug. Solid solutions of active ingredient and solubilizer are used in particular.

It is possible to employ for parenteral administration besides solubilizers also emulsions, for example fatty emulsions. The claimed copolymers are also suitable for processing a slightly soluble drug for this purpose.

Pharmaceutical formulations of the abovementioned type can be obtained by processing the claimed copolymers with active pharmaceutical ingredients by conventional methods and with use of known and novel active ingredients.

The application of the invention may additionally comprise pharmaceutical excipients and/or diluents. Excipients which are particularly mentioned are cosolvents, stabilizers, preservatives.

The active pharmaceutical ingredients used are insoluble or sparingly soluble in water. According to DAB 9 (German Pharmacopeia), the solubility of active pharmaceutical ingredients is categorized as follows: sparingly soluble (soluble in 30 to 100 parts of solvent); slightly soluble (soluble in 100 to 1000 parts of solvent); practically insoluble (soluble in more than 10 000 parts of solvent). The active ingredients may in this connection come from any range of indications.

Examples which may be mentioned here are benzodiazepines, antihypertensives, vitamins, cytostatics—especially Taxol, anesthetics, neuroleptics, antidepressants, agents having antiviral activity, such as, for example, agents having anti-HIV activity, antibiotics, antimycotics, antidementia agents, fungicides, chemotherapeutics, urologicals, platelet aggregation inhibitors, sulfonamides, spasmolytics, hormones, immunoglobulins, sera, thyroid therapeutics, psychoactive drugs, antiparkinson agents and other antihyperkinetics, opthalmologicals, neuropathy products, calcium metabolism regulators, muscle relaxants, anesthetics, lipid-lowering agents, hepatotherapeutics, coronary agents, cardiac agents, immunotherapeutics, regulatory peptides and their inhibitors, hypnotics, sedatives, gynecologicals, gout remedies, fibrinolytics, enzyme products and transport proteins, enzyme inhibitors, emetics, blood flow stimulators, diuretics, diagnostic aids, corticoids, cholinergics, biliary therapeutics, anti asthmatics, bronchodilators, beta-receptor blockers, calcium antagonists, ACE inhibitors, arteriosclerosis remedies, antiinflammatory drugs, anticoagulants, antihypertensives, antihypoglycemics, antihypertensives, antifibrinolytics, antiepileptics, antiemetics, antidotes, antidiabetics, antiarrhythmics, antianemics, antiallergics, anthelmintics, analgesics, analeptics, aldosterone antagonists, slimming agents.

One possible production variant is to dissolve the solubilizer in the aqueous phase, if appropriate with gentle heating, and subsequently to dissolve the active ingredient in the aqueous solubilizer solution. It is likewise possible to dissolve solubilizer and active ingredient simultaneously in the aqueous phase.

It is also possible to use the copolymers of the invention as solubilizer for example by dispersing the active ingredient in the solubilizer, if appropriate with heating, and mixing with water while stirring.

A further possibility is for the solubilizers to be processed in the melt with the active ingredients. It is possible in this way in particular to obtain solid solutions. Also suitable for this purpose is the melt extrusion process, inter alia. A further possibility for producing solid solutions is also to prepare solutions of solubilizer and active ingredient in suitable organic solvents and subsequently to remove the solvent by usual processes.

The invention therefore also relates in general to pharmaceutical preparations which comprise at least one of the copolymers of the invention as solubilizer. Preferred preparations are those which, besides the solubilizer, comprise an active pharmaceutical ingredient which is slightly soluble for insoluble in water, for example from the abovementioned areas of indication.

Particularly preferred pharmaceutical preparations from those mentioned above are formulations which can be administered orally.

The content of solubilizer of the invention of the pharmaceutical preparation is in the range from 1 to 75% by weight, preferably 5 to 60% by weight, particularly preferably 5 to 50% by weight, depending on the active ingredient.

A further particularly preferred embodiment relates to pharmaceutical preparations in which the active ingredients and the solubilizer are present as solid solution. In this case, the ratio of solubilizers to active ingredient is preferably from 1:1 to 4:1 by weight, but may be up to 100:1, in particular up to 15:1. The only concerns are that when the finished drug form is used firstly the amount of active ingredient present in the drug form is effective, and secondly the forms are not too large in the case of oral drug forms.

Solubilizers for Food Preparations:

Besides use in cosmetics and pharmacy, the copolymers of the invention are also suitable as solubilizers in the food sector for nutritional substances, auxiliaries or additives which are slightly soluble or insoluble in water, such as, for example, fat-soluble vitamins or carotenoids. Examples which may be mentioned are beverages colored with carotenoids.

Solubilizers for Crop Protection Preparations:

Use of the copolymers of the invention as solubilizers in agrochemistry may comprise inter alia formulations which comprise pesticides, herbicides, fungicides or insecticides, especially including preparations of crop protection agents employed as formulations for spraying or watering.

The copolymers of the invention are distinguished by a particularly good solubilizing effect. They are also able to form so-called solid solutions with slightly soluble substances. Solid solutions refer according to the invention to systems in which no portions of the slightly soluble substance are evidently crystalline on visual inspection. There are furthermore no evidently amorphous constituents on visual inspection of the stable solid solutions. The visual inspection takes place using a light microscope at 40× magnification.

The preparation and use of the copolymers of the invention is explained in more detail in the following examples.

Preparation of the Copolymers

Abbreviations Used:

VCap: N-vinylcaprolactam

VP: N-vinylpyrrolidone

VAc: vinyl acetate

PEG: polyethylene glycol

EXAMPLE 1

| Initial charge: | 165.0 g of ethyl acetate, |
| | 100.0 g of PEG 6000, |
| | 20.0 g of vinyl acetate, |
| | 10.50 g of feed 2 |
| Feed 1: | 500 g of vinylcaprolactam |
| | 180 g of vinyl acetate |
| | 100 g of ethyl acetate |
| Feed 2: | 10.50 g of tert-butyl perethylhexanoate |
| | (98% by weight pure) |
| | 94.50 g of ethyl acetate |

The initial charge was heated in a stirred apparatus without the portion of feed 2 under an $N_2$ atmosphere to 77° C. When the internal temperature of 77° C. was reached, the portion of feed 2 was added and initial polymerization was carried out for 15 min. Subsequently, feed 1 was metered in over the course of 5 h and feed 2 over the course of 2 h. After all the feeds had been metered in, the reaction mixture was polymerized for a further 3 h. After the further polymerization, the reaction mixture was diluted with 500 ml of water. Volatile constituents were removed by steam distillation. The aqueous solution was freeze dried. The copolymers were obtained after grinding as very free-flowing powders.

The further copolymers of examples 2-5 were prepared analogously with slightly modified composition.

EXAMPLE 2

| Initial charge: | 165 g of ethyl acetate |
| --- | --- |
| | 100.0 g of PEG 6000 |
| | 22.0 g of vinyl acetate |
| | 10.50 g of feed 2 |
| Feed 1: | 480 g of vinylcaprolactam |
| | 198 g of vinyl acetate |
| | 100 g of ethyl acetate |
| Feed 2: | 10.50 g of tert-butyl perethylhexanoate |
| | (98% by weight pure) |
| | 94.50 g of ethyl acetate |

EXAMPLE 3

| Initial charge: | 25 g of ethyl acetate |
| --- | --- |
| | 104.0 g of PEG 6000, |
| | 1.0 g of feed 2 |
| Feed 1: | 240 g of vinyl acetate |
| Feed 2: | 456 g of vinylcaprolactam |
| | 240 g of ethyl acetate |
| Feed 3: | 10.44 g of tert-butyl perpivalate |
| | (75% by weight pure in a mixture of aliphatics) |
| | 67.90 g of ethyl acetate |

EXAMPLE 4

| Initial charge: | 25 g of ethyl acetate |
| --- | --- |
| | 112.0 g of PEG 6000, |
| | 1.0 g of feed 2 |
| Feed 1: | 408 g of vinylcaprolactam |
| | 280 g of vinyl acetate |
| | 240 g of ethyl acetate |
| Feed 2: | 10.32 g of tert-butyl perpivalate |
| | (75% by weight pure in a mixture of aliphatics) |
| | 67.10 g of ethyl acetate |

EXAMPLE 5

| Initial charge: | 25 g of ethyl acetate, |
| --- | --- |
| | 112.0 g of PEG 6000, |
| | 1.0 g of feed 2 |
| Feed 1: | 428.0 g of vinylcaprolactam |
| | 260 g of vinyl acetate |
| | 240 g of ethyl acetate |
| Feed 2: | 10.32 g of tert-butyl perpivalate |
| | (75% by weight pure in a mixture of aliphatics) |
| | 67.10 g of ethyl acetate |

| | Composition in % by weight | | | K value |
| --- | --- | --- | --- | --- |
| Example No. | PEG 6000 | VCap | VAc | (1% by weight in ethanol) |
| 1 | 12.5 | 62.5 | 25 | 18.5 |
| 2 | 12.5 | 60 | 27.5 | 40.4 |
| 3 | 13 | 57 | 30 | 19.8 |
| 4 | 14 | 51 | 35 | 25.2 |
| 5 | 14 | 53.5 | 32.5 | 22.4 |

EXAMPLE 6

| Initial charge: | 50 g of butyl acetate, 150.0 g of PEG 6000, |
| --- | --- |
| | 1.0 g of feed 3 |
| Feed 1: | 500 g of VCap, 120.0 g of butyl acetate |
| Feed 2: | 350.0 g of VAc, 80.0 g of butyl acetate |
| Feed 3: | 12.75 g of tert-butyl perpivalate |
| | (75% by weight in aliphatic mixture), |
| | 117.25 g of butyl acetate |

The initial charge was heated in a stirred apparatus under an $N_2$ atmosphere to 77° C. When the temperature was reached, feed 1, feed 2 and feed 3 were started. Feed 1 was metered in over the course of 5 h, feed 2 was metered in over the course of 2 h and feed 3 was metered in over the course of 5.5 h. After all the feeds had been metered in, the reaction mixture was polymerized for a further 4 h. After the further polymerization, the reaction mixture was diluted with 500 ml of solvent. Volatile constituents were removed by steam distillation. The aqueous solution was freeze dried. The copolymers were obtained after grinding as very free-flowing powders.

The copolymers of Examples 7 to 17 were prepared analogously.

| | Composition in % by weight | | | K value |
| --- | --- | --- | --- | --- |
| Example No. | PEG 6000 | VCap | VAc | (1% by weight in ethanol) |
| 6 | 15 | 50 | 35 | 32.2 |
| 7 | 20 | 50 | 30 | 21.7 |
| 8 | 25 | 50 | 25 | 22.7 |
| 9 | 30 | 50 | 20 | 23.6 |
| 10 | 35 | 50 | 15 | 25.1 |
| 11 | 50 | 40 | 10 | 24.3 |

| | Composition in % by weight | | | K value |
| --- | --- | --- | --- | --- |
| Example No. | PEG 1500 | VCap | VAc | (1% by weight in ethanol) |
| 12 | 15 | 50 | 35 | 32.2 |
| 13 | 25 | 50 | 25 | 23.1 |
| 14 | 35 | 50 | 15 | 29.7 |

| Example No. | Composition in % by weight | | | K value (1% by weight in ethanol) |
| --- | --- | --- | --- | --- |
| 15 | PEG 9000 15 | VCap 50 | VAc 35 | 30.5 |
| 16 | PEG 1500 20 | VP 60 | VAc 20 | 35.6 |

-continued

| 17 | PEG 6000 20 | VP 60 | VAc 20 | 35.8 |

EXAMPLE 18

| Initial charge: | 40 g of ethyl acetate, 120.0 g of PEG 6000, 1.28 g of feed 2 |
| --- | --- |
| Feed 1: | 400 g of VCap, 280.0 g of vinyl acetate, 225.0 g of ethyl acetate |
| Feed 2: | 10.2 g of tert-butyl perpivalate (75% by weight pure in mixture of aliphatics), 118.4 g of ethyl acetate |

The initial charge was heated in a stirred apparatus under an $N_2$ atmosphere to 77° C. When the temperature was reached, the feeds were started. Feed 1 was metered in over the course of 5 h and feed 2 over the course of 5.5 h. After all the feeds had been metered in, the reaction mixture was polymerized for a further 3 h. After the further polymerization, the reaction mixture was diluted with about 500 ml of solvent. Volatile constituents were removed by steam distillation. The aqueous solution was freeze dried. The copolymers were obtained after grinding as very free-flowing powders.

EXAMPLE 19

Analogous to example 18, but with tert-butyl perethylhexanoate at a bath temperature of 85° C.

EXAMPLE 20

Analogous to example 19, but with the following feeds:

| Initial charge: | 120.0 g of PEG 6000 |
| --- | --- |
| Feed 1: | 160 g of VCap, 280.0 g of vinyl acetate, 50.0 g of ethyl acetate |
| Feed 2: | 10.2 g of tert-butyl perpivalate (75% by weight pure in mixture of aliphatics), 91.80 g of ethyl acetate |
| Feed 3: | 240 g of VCap, 242.0 g of ethyl acetate |

Feed 1 was added over the course of 2 h and feed 2 over the course of 5.5 h. Feed 3 was started immediately after the end of feed 1.

EXAMPLE 21

Analogous to example 19, monomer composition in % by weight: 15 PEG/55 VCap/30 Vac.

EXAMPLE 22

Analogous to example 19, with tert-butanol as solvent.

EXAMPLE 23

Analogous to example 18, after the end of the further polymerization 9.07 g of tert-butyl perpivalate in 81.6 g of ethyl acetate were added, followed by further polymerization for 2 h to reduce residual monomers.

EXAMPLE 24

Analogous to example 21, but with monomer composition in % by weight: 15 PEG/50 VCap/35 VAc, doubled quantities and in a pressure apparatus at 90° C. A pressure in the region of 0.2 MPa was set up in this case.

EXAMPLE 25

Spray Drying

A polymer prepared in analogy to example 18 was spray dried. The drying took place straightforwardly.

| Atomizer: | two-fluid nozzle, 1.3 mm Teflon |
| --- | --- |
| Additive: | none |
| Solids content: | 15% by weight |
| Inlet temp.: | 121° C. |
| Outlet temp.: | 55° C. |
| Yield: | 77% |
| Color: | white |
| Powder property: | slightly blocked |

Addition of colloidal silica as spraying aid (additive) improved the already good properties and afforded a free-flowing powder.

EXAMPLE 26

An aqueous polymer solution obtained as in example 1 was processed by spray drying in analogy to example 25.

COMPARATIVE EXAMPLES

For comparison, the graft copolymers described in EP-A 953 437 (Examples 1, 3; Table 1) of the following composition were prepared:

Comparative Example A

70% by weight of VAc, 30% by weight of PEG 6000

Comparative Example B

70% by weight of VAc, 30% by weight of PEG 1500
These polymers exhibited noticeable tackiness.
Preparation of Solid Solutions: General Procedure The polymer-active ingredient mixture was produced by weighing the active ingredient and the polymer in the ratio 1:1 by weight into a suitable glass vessel (2 g of each) and then adding 16 ml of dimethylformamide as solvent. The mixture was stirred with a magnetic stirrer at 20° C. for 24 hours. The solution was then applied to a glass plate using a 120 μm knife. This plate was dried under a hood at RT for 0.5 hour and then dried in a drying oven at 50° C. and 10 mbar for a further 0.5 hour in order to remove the solvent quantitatively. The samples were subsequently inspected visually. If the films were clear and the active ingredient did not crystallize after 7 days, the active ingredient was assessed as stably dissolved in the polymer (indication in Table 1:50). If no solid solution could be obtained with an active ingredient content of 50% by weight, the experiment was repeated with an active ingredient loading of 33% by weight, and the formation of a stable solid solution was assessed as above (indication in Table: 33).

Stability of a Solid Solution

| | Copolymer of Example No./Content of active ingredient [% by weight] | | | | |
|---|---|---|---|---|---|
| Solid solution of carbamazepine | 1/50 | 2/50 | 3/50 | 4/33 | 5/50 |

| | Copolymer of Example No./Content of active ingredient [% by weight] | | | |
|---|---|---|---|---|
| Solid solution of estradiol | 1/50 | 2/50 | 3/50 | 4/50 |

| | Copolymer of Example No./Content of active ingredient [% by weight] | | | | |
|---|---|---|---|---|---|
| Solid solution of piroxicam | 1/33 | 2/33 | 3/33 | 4/33 | 5/33 |

| | Copolymer of Example No./Solubilization at 20°C. in [g/100 ml] | | | | |
|---|---|---|---|---|---|
| Solid solution of clotrimazole | 1/50 | 2/50 | 3/50 | 4/33 | 5/50 |

| | Copolymer of Example No./Content of active ingredient [% by weight] | | | | | | |
|---|---|---|---|---|---|---|---|
| Solid solution of carbamazepine | 6/50 | 7/50 | 8/50 | 12/33 | 13/50 | 14/50 | 15/33 |

| | Copolymer of Example No./Content of active ingredient [% by weight] | | | | | | | |
|---|---|---|---|---|---|---|---|---|
| Solid solution of estradiol | 6/50 | 7/50 | 8/50 | 9/50 | 10/50 | 12/50 | 14/50 | 15/33 |

| | Copolymer of Example No./Content of active ingredient [% by weight] | | |
|---|---|---|---|
| Solid solution of piroxicam | 12/33 | 13/33 | 15/33 |

| | Copolymer of Example No./Content of active ingredient [% by weight] | | | | | | | | | |
|---|---|---|---|---|---|---|---|---|---|---|
| Solid solution of clotrimazole | 6/50 | 7/50 | 8/50 | 9/50 | 10/50 | 11/33 | 12/50 | 13/33 | 14/50 | 15/33 | 16/50 |

| | Copolymer of Example No./Content of active ingredient [% by weight] | | | | | |
|---|---|---|---|---|---|---|
| Solid solution of carbamazepine | 18/50 | 19/50 | 20/50 | 21/33 | 22/50 | 24/50 |

| | Copolymer of Example No./Content of active ingredient [% by weight] | | | | | |
|---|---|---|---|---|---|---|
| Solid solution of estradiol | 18/50 | 19/50 | 20/50 | 21/50 | 22/50 | 24/50 |

| | Copolymer of Example No./Content of active ingredient [% by weight] | | | | | |
|---|---|---|---|---|---|---|
| Solid solution of piroxicam | 18/33 | 19/33 | 20/33 | 21/33 | 22/33 | 24/33 |

| | Copolymer of Example No./Content of active ingredient [% by weight] | | | | | |
|---|---|---|---|---|---|---|
| Solid solution of clotrimazole | 18/50 | 19/50 | 20/50 | 21/33 | 22/50 | 24/50 |

No stable solid solutions were obtainable with the polymers of Comparative Examples A and B.

Preparation of Solubilizates 2 g of the copolymer were weighed into a glass beaker. A drug was then weighed into each mixture in order to obtain a supersaturated solution, as follows. If the mass weighed in dissolved in the medium, the weight was increased until a sediment formed. Amount of active ingredient weighed in: 17-β-estradiol 0.2 g; piroxicam 0.2; clotrimazole 0.2 g; carbamazepine 0.3 g; ketoconazole 0.25 g; griseofulvin 0.25 g; cinnarizine 0.25 g.

Phosphate buffer of pH 7.0 was then added until solubilizer and phosphate buffer were present in the ratio of 1:10 by weight. A magnetic stirrer was used to stir this mixture at 20° C. for 72 hours. A resting period of at least 1 hour followed. The mixture was filtered and then measured by photometry, and the content of active ingredient was determined.

| | Copolymer of Ex. No./Solubilization at 20° C. in [g/100 ml] | | | | |
|---|---|---|---|---|---|
| Carbamazepine | 1/0.04 | 2/.07 | 3/0.40 | 4/0.28 | 5/0.26 |

| | Copolymer of Ex. No./Solubilization at 20° C. in [g/100 ml] | | | |
|---|---|---|---|---|
| Estradiol | 1/0.05 | 3/0.23 | 4/0.33 | 5/0.25 |

| | Copolymer of Ex. No./Solubilization at 20° C. in [g/100 ml] | | | | |
|---|---|---|---|---|---|
| Piroxicam | 1/0.11 | 2/0.18 | 3/0.28 | 4/0.09 | 5/0.13 |

| | Copolymer of Ex. No./Solubilization at 20° C. in [g/100 ml] | | | |
|---|---|---|---|---|
| Clotrimazole | 1/0.01 | 2/0.01 | 3/0.17 | 4/0.15 |

| | Copolymer of Ex. No. /Solubilization at 20° C. in [g/100 ml] | | | | | | | | | | |
|---|---|---|---|---|---|---|---|---|---|---|---|
| Carbamazepine | 6/0.31 | 7/0.35 | 8/0.22 | 9/0.22 | 10/0.19 | 11/0.19 | 12/0.26 | 13/0.12 | 14/0.17 | A/0.10 | B/0.11 |

| | Copolymer of Ex. No./Solubilization at 20° C. in [g/100 ml] | | | | | | | |
|---|---|---|---|---|---|---|---|---|
| Estradiol | 6/0.23 | 7/0.18 | 8/0.17 | 9/0.09 | 10/0.09 | 14/0.04 | A/0.07 | B/0.11 |

| | Copolymer of Ex. No./Solubilization at 20° C. in [g/100 ml] | | | | | | | | | | |
|---|---|---|---|---|---|---|---|---|---|---|---|
| Piroxicam | 6/0.45 | 7/0.45 | 8/0.44 | 9/0.42 | 10/0.44 | 11/0.39 | 12/0.45 | 14/0.42 | 16/0.37 | 17/0.4 | A/0.10 | B/0.27 |

| | Copolymer of Ex. No./Solubilization at 20° C. in [g/100 ml] | | | |
|---|---|---|---|---|
| Clotrimazole | 6/0.11 | 7/0.10 | 8/0.06 | 9/0.07 |

| | Copolymer of Ex. No./Solubilization at 20° C. in [g/100 ml] | | | |
|---|---|---|---|---|
| Carbamazepine | 18/0.31 | 19/0.25 | 20/0.28 | 21/0.27 |

| | Copolymer of Ex. No./Solubilization at 20° C. in [g/100 ml] | | | | | |
|---|---|---|---|---|---|---|
| Estradiol | 18/0.26 | 19/0.23 | 20/0.22 | 21/0.23 | 22/0.26 | 24/0.32 |

| | Copolymer of Ex. No./Solubilization at 20° C. in [g/100 ml] | | | | | |
|---|---|---|---|---|---|---|
| Piroxicam | 18/0.17 | 19/0.09 | 20/0.41 | 21/0.19 | 22/0.16 | 24/0.10 |

| | Copolymer of Ex. No./Solubilization at 20° C. in [g/100 ml] | | | | |
|---|---|---|---|---|---|
| Clotrimazole | 18/0.06 | 19/0.13 | 20/0.18 | 21/0.12 | 22/0.13 |

| | Solubilization at 20° C. in [g/100 ml] | | |
|---|---|---|---|
| Copolymer of Ex. 6 | ketoconazole 0.11 | griseofulvin 0.31 | cinnarizine 0.02 |

The solubilization at 37° C. was determined in analogy to the method described above.

| | Copolymer of Ex. No./Solubilization at 37° C. in [g/100 ml] | | |
|---|---|---|---|
| Carbamazepine | 1/0.36 | 7/0.93 | 9/0.26 |

| | Copolymer of Ex. No./Solubilization at 37° C. in [g/100 ml] | | |
|---|---|---|---|
| Piroxicam | 1/0.51 | 7/1.04 | 9/0.55 |

| | Copolymer of Ex. No./Solubilization at 37° C. in [g/100 ml] | |
|---|---|---|
| Estradiol | 1/0.99 | 9/0.07 |

| | Copolymer of Ex. No./Solubilization at 37° C. in [g/100 ml] |
|---|---|
| Clotrimazole | 1/0.17 |

Determination of the Glass Transition Temperatures Tg as Measure of the Tack-Free Processability:

| $T_g$[°C.] | Copolymer of Ex. 1 | Copolymer of Comp. Ex. A | Copolymer of Comp. Ex. B |
|---|---|---|---|
| | +54 | −32 | −40 |

In addition, the release behavior of solid solutions of the invention composed of solubilizer polymer and active ingredient (with carbamazepine as example)—formulated in a tablet—was compared with the release behavior of a tablet which comprises only active ingredient without solubilizer polymer. The following tablet compositions were used for this:

Formulation A: Solid Solution

| Materials | mg/Tablet | [%] |
|---|---|---|
| Solid solution | 250 | 50 |
| Microcrystalline cellulose | 230 | 46 |
| Carboxymethylcellulose sodium, crosslinked | 15 | 3 |
| Colloidal silica | 2.5 | 0.5 |
| Magnesium stearate | 2.5 | 0.5 |
| Total: | 500 | 100 |

Formulation B: Active Ingredient without Polymer (CBZ)

| Materials | mg/Tablet | [%]t |
|---|---|---|
| Carbamazepine | 75 | 15 |
| Lactose | 175 | 35 |
| Microcrystalline cellulose | 230 | 46 |
| Carboxymethylcellulose sodium, crosslinked | 15 | 3 |
| Colloidal silica | 2.5 | 0.5 |
| Magnesium stearate | 2.5 | 0.5 |
| Total | 500 | 100 |

The solid solution was powdered in a mortar; the particle size was in the region of 200 μm. The further excipients with the exception of the magnesium stearate are added as indicated in the table and mixed in a Turbula mixer for 10 minutes. The mass of magnesium stearate indicated in the table is then added and mixed again in the Turbula mixer for 2 minutes. The mixture was tableted in an EK 0 excentric press with a 12 mm punch under a compressive force of 15 kN.

The release from the tablets was determined in 0.08 M HCl (300 ml) at 22° C. Samples were filtered through a 10 μm filter and the carbamazepine content was determined by UV spectrometry at 286 nm.

| Time [min] | CBZ release [%] | Solid solution release [%] |
|---|---|---|
| 0 | 0 | 0 |
| 10 | | 96 |
| 20 | 43 | 99 |
| 40 | 48 | 100 |
| 60 | 50 | 102 |
| 90 | 50 | 99 |
| 120 | 50 | 100 |

We claim:

1. A method comprising solubilizing a slightly water soluble substance with a copolymer wherein the copolymer solubilizes the slightly water-soluble substance and wherein the copolymer is obtained by free-radical polymerization of a mixture of
   i) 30 to 80% by weight of N-vinylcaprolactam, N-vinylpyrrolidone, or a mixture thereof,
   ii) 10 to 50% by weight of vinyl acetate, and
   iii) 10 to 50% by weight of a polyethylene glycol,
   1. with the proviso that the total of components i), ii) and iii) equals 100% by weight.

2. The method according to claim 1, where the copolymer is obtained from
   i) 30 to 70% by weight of N-vinylcaprolactam, N-vinylpyrrolidone, or a mixture thereof,
   ii) 15 to 35% by weight of vinyl acetate, and
   iii) 10 to 35% by weight of a polyethylene glycol.

3. The method according to claim 1, where N-vinylcaprolactam is employed as component i).

4. The method according to claim 1, where the copolymer comprises a polyethylene glycol having a molecular weight of from 1000 daltons to 10 000 daltons as component iii).

5. The method according to claim 1, where the copolymer has a K value from 10 to 60 and wherein the K value is measured in a 1% by weight ethanolic solution.

6. The method according to claim 4, where the copolymer has a K value of from 15 to 40 and wherein the K value is measured in a 1% by weight ethanolic solution.

7. The method according to claim 1, where the slightly water-soluble substance is a bioactive substance.

8. The method according to claim 1 for producing a pharmaceutical preparation for the treatment of diseases.

9. The method according to claim 1 for producing cosmetic preparations.

10. The method according to claim 1 for producing-agrochemical preparations.

11. The method according to claim 1 for producing-dietary supplements or dietetic compositions.

12. The method according to claim 1 for producing food products.

13. The method according to claim 1 for producing colorant preparations.

* * * * *